(12) United States Patent
Perez-Cruet

(10) Patent No.: US 8,192,443 B2
(45) Date of Patent: Jun. 5, 2012

(54) PEDICLE ACCESS DEVICE

(75) Inventor: Mick J. Perez-Cruet, Bloomfield, MI (US)

(73) Assignee: Mi4Spine, LLC, Bloomfield Hills, MI (US)

( * ) Notice: Subject to any disclaimer, the term of this patent is extended or adjusted under 35 U.S.C. 154(b) by 1582 days.

(21) Appl. No.: 11/408,571

(22) Filed: Apr. 21, 2006

(65) Prior Publication Data

US 2007/0270896 A1 Nov. 22, 2007

(51) Int. Cl.
*A61B 17/58* (2006.01)
*A61B 17/32* (2006.01)

(52) U.S. Cl. ............... 606/96; 600/164.01; 600/164.04; 600/264; 606/181

(58) Field of Classification Search .................. 604/264, 604/164.04, 164.01; 606/96, 181; 600/190, 600/210, 214
See application file for complete search history.

(56) References Cited

U.S. PATENT DOCUMENTS

| | | | | |
|---|---|---|---|---|
| 4,443,941 A | * | 4/1984 | McPhaul | 606/101 |
| 4,708,147 A | * | 11/1987 | Haaga | 600/566 |
| 5,263,937 A | * | 11/1993 | Shipp | 604/166.01 |
| 5,352,206 A | * | 10/1994 | Cushieri et al. | 604/170.01 |
| 5,423,824 A | * | 6/1995 | Akerfeldt et al. | 606/80 |
| 5,649,946 A | * | 7/1997 | Bramlet | 606/167 |
| 5,693,031 A | * | 12/1997 | Ryan et al. | 604/167.03 |
| 6,656,189 B1 | * | 12/2003 | Wilson et al. | 606/97 |
| 2005/0033307 A1 | * | 2/2005 | Cook et al. | 606/104 |

* cited by examiner

*Primary Examiner* — Eduardo C Robert
*Assistant Examiner* — Julianna N Harvey
(74) *Attorney, Agent, or Firm* — John A. Miller; Miller IP Group, PLC

(57) ABSTRACT

A pedicle access device that has particular application for positioning a pedicle screw during a minimally invasive spinal fusion surgical procedure. The pedicle access device includes a positioning needle having a hollow tube and a specially designed tip that conforms with a facet complex of a vertebra proximate a pedicle. A targeting needle having a pointed end is inserted through the hollow tube of the positioning needle, and is secured thereto so the tip of the targeting needle extends out of the end of the positioning needle. The tip of the targeting needle allows the positioning needle to be accurately positioned on the pedicle, and the specially configured tip of the positioning needle allows it to be secured thereto without slipping.

21 Claims, 4 Drawing Sheets

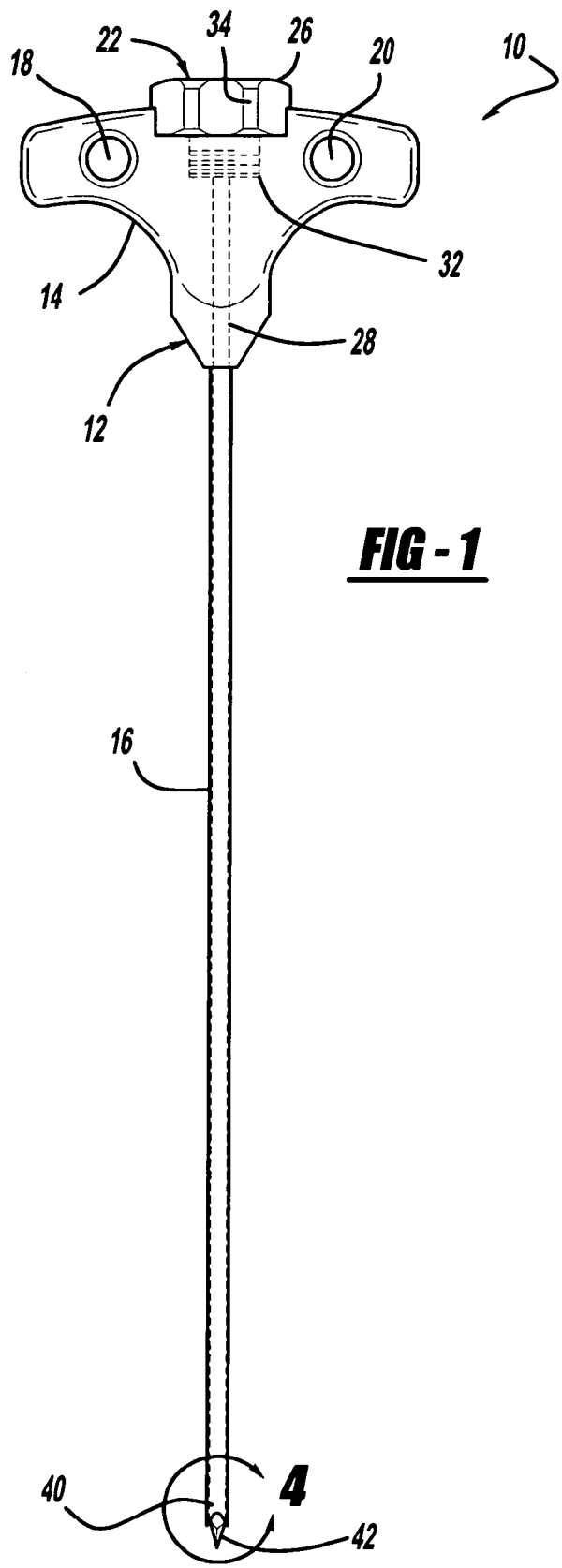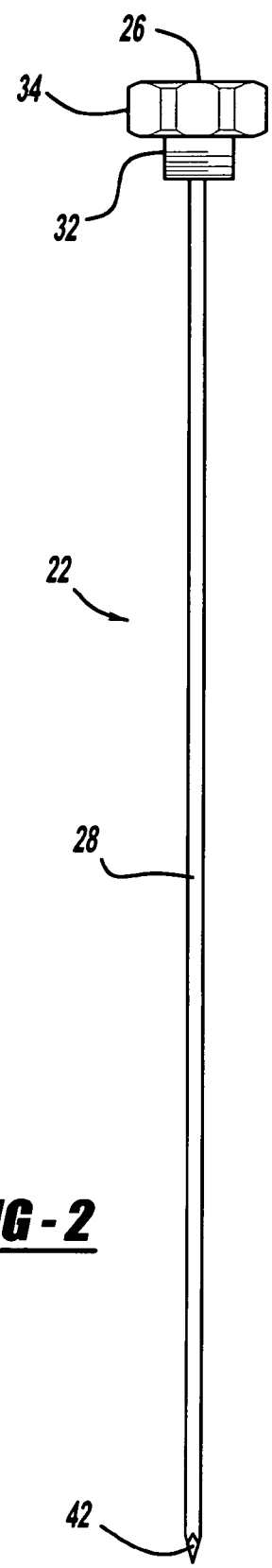

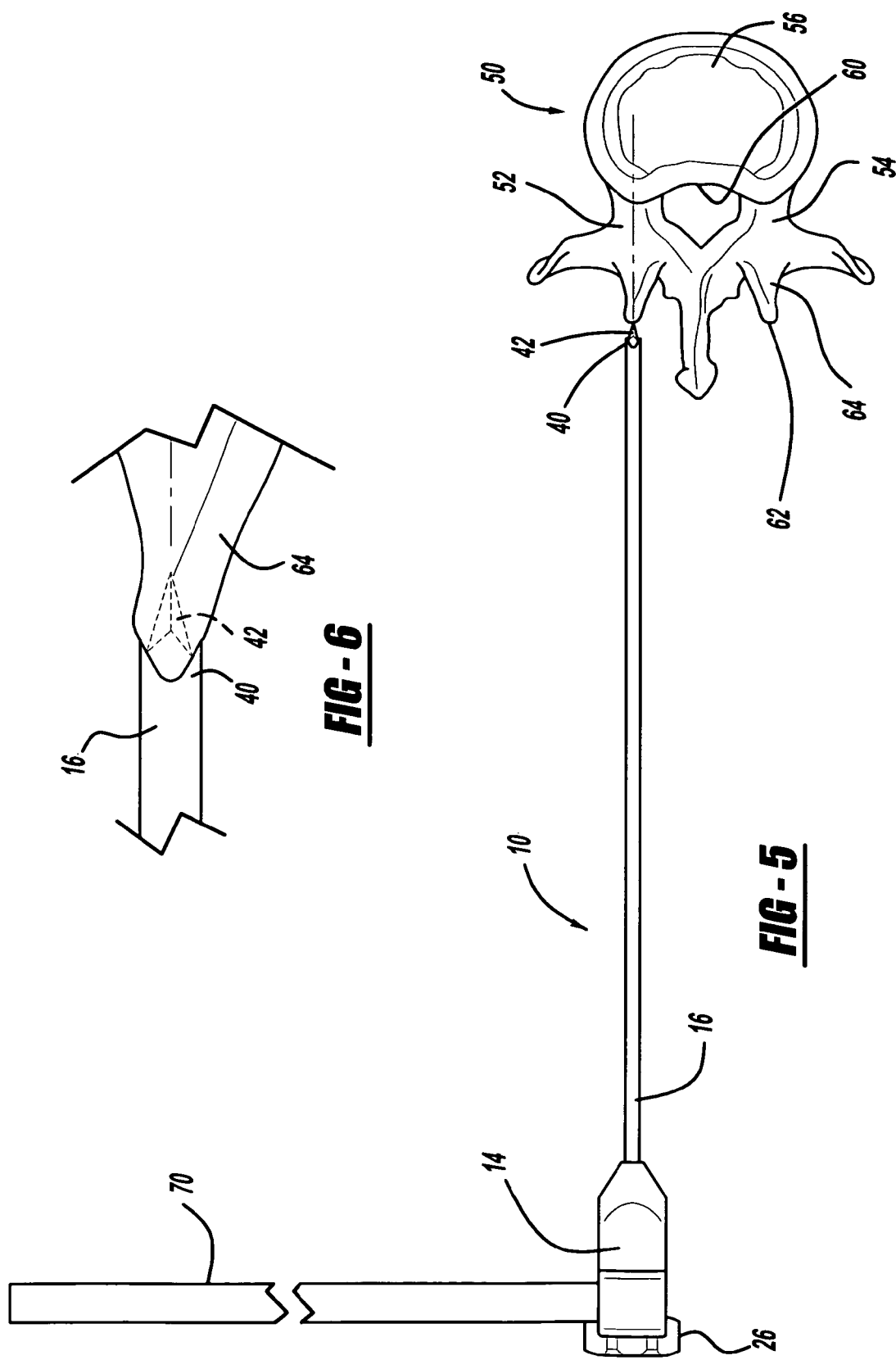

PEDICLE ACCESS DEVICE

BACKGROUND OF THE INVENTION

1. Field of the Invention

This invention relates generally to a device for accessing the pedicle of a vertebra during a surgical procedure and, more particularly, to a device having a specially configured tip for docking to a facet complex of a vertebra during spinal instrumentation and fusion surgery, where the device includes a hollow rod for passing a K-wire through.

2. Discussion of the Related Art

The human spine includes a series of vertebrae interconnected by connective tissue referred to as disks that act as a cushion between the vertebrae. The disks allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal disks, abnormal spinal curvature and a weak or unstable spine.

In an attempt to preserve normal anatomical structures during spine surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filed with the graft material. This procedure is referred to as interbody fusion since it is between adjacent vertebrae. The cage includes holes that allow the vertebrae and the graft material to grow together to provide the fusion. The cage supports the weight of adjacent vertebrae while the fusion is occurring through the cage. Alternatively, the bone graft material can be placed directly over or lateral to the spine, referred to as postero-lateral fusion. Typically the bone graft material is autogenous bone material taken from the patient, or allograft bone material harvested from cadavers. Synthetic bone materials can also be used as the graft material. Generally, the patient's own bone material offers the best fusion material and is the current "gold standard".

Spinal instrumentation is then performed to immobilize the vertebral segments where the bone is placed. Similar to the function of wearing a cast or brace after breaking a long bone, spinal instrumentation allows for immobilization which promotes bone fusion. One of the most common forms of spinal instrumentation is the pedicle screw and rod construct. The rods, which span adjacent vertebrae, are mounted to the vertebra using pedicle screws that are threaded through the pedicles of each vertebra and into the vertebral body. Accurate placement of the pedicle screws relative to the vertebral pedicle is very important to prevent injury to nerves or spinal cord. Typically, fluoroscopy is used to ensure that the pedicle screws are properly oriented relative to the pedicle.

In traditional open pedicle screw instrumentation, the muscles are stripped off the bony anatomy of the spine to expose the facet and transverse process for accurate pedicle screw placement. This results in significant muscle and ligamentous damage resulting in signficant post-operative pain and discomfort for patients and often extending hospital stays. Recovery times can be extended and additional problems at adjacent levels of the spine can ultimately result in more surgery.

Recently, minimally invasive spine instrumentation techniques have been developed to perform percutaneous pedicle screw instrumentation. In this procedure, pedicle screws and rods can be placed without stripping the muscles and ligaments off the spine. This results in significant recovery benefits for patients undergoing spine fusion and instrumentation. Since the normal anatomical integrity of the spine is maintained, long term spine health is improved.

In one known process of percutaneous pedicle screw instrumentation, a Jamshidi needle is used to dock on to the junction of the vertebrae between the facet complex and the transverse process of the vertebra. Gentle taps with a mallet cause the Jamshidi needle to be advanced through the pedicle, making sure not to cross the medial border of the pedicle, which can result in nerve root injury, until the junction between the pedicle base and the vertebral body is reached. Fluoroscopic visualization into the anterior posterior and lateral planes of the vertebra is used to see the orientation of the Jamshidi needle. The correct trajectory of the Jamshidi needle should place the tip of the needle in the center of the pedicle in the anterior posterior view when the tip of the Jamshidi needle lies at the pedicle vertebral body junction in the lateral view.

Once the junction between the base of the pedicle wall and the vertebral body is reached, the Jamshidi needle can be directed in a more medial fashion. The Jamshidi needle is typically passed to about one-half the depth of the vertebral body, and then a K-wire is passed down the Jamshidi needle and into the vertebral body a little farther to seat it into the bone. The Jamshidi needle is then removed. A series of canulated muscle dilators are then passed over the K-wire to prevent the soft tissue from going into the threads of the tap and a pedicle screw is then passed down the dilators. The pedicle is tapped and the appropriate size pedicle screw is placed.

The procedure described above has a number of limitations. For example, the tip of the Jamshidi needle tends to slide off of the facet of the vertebra making specific targeting of the pedicle difficult. Further, the Jamshidi needle needs to be passed through the pedicle in a lateral to medial direction providing the risk of injury to neural elements. Also, when removing the Jamshidi needle the K-wire can become dislodged requiring re-cannulation of the pedicle with the Jamshidi needle.

SUMMARY OF THE INVENTION

In accordance with the teachings of the present invention, a pedicle access device is disclosed that has particular application for positioning a pedicle screw during a minimally invasive spinal fusion surgical procedure. The pedicle access device includes a positioning needle having a hollow tube and a specially designed tip that conforms with the superior facet of a vertebra proximate a pedicle. A targeting needle having a pointed end is inserted through the hollow tube of the positioning needle, and is secured thereto so the tip of the targeting needle extends out of the end of the positioning needle. The tip of the targeting needle allows the positioning needle to be accurately positioned on the superior facet, and the specially configured tip of the positioning needle allows it to be secured thereto without slipping.

The targeting needle is then removed from the positioning needle, and a K-wire is passed through the positioning needle into the vertebral body of the vertebra. The positioning needle is then removed, a series of dilators are passed over the K-wire and the pedicle is tapped to expand the hole in the pedicle to the desired size. A cannulated pedicle screw is then passed over the K-wire, and threaded into the hole through the pedicle and into the vertebral body. The pedicle access device may include an extended rod that is coupled to the positioning needle so that the surgeon's hand can be separated from the access device during X-rays, thus reducing x-ray exposure to the surgeon.

Additional features of the present invention will become apparent from the following description and appended claims, taken in conjunction with the accompanying drawings.

BRIEF DESCRIPTION OF THE DRAWINGS

FIG. 1 is a side view of a pedicle access device, according to an embodiment of the present invention;

FIG. 2 is a side view of a targeting needle of the pedicle access device shown in FIG. 1 removed from a positioning needle;

FIG. 5 is a perspective view of the pedicle access device positioned adjacent to a lumbar vertebra, and including an extended handle for holding the pedicle access device during the surgical procedure;

FIG. 6 is a broken-away, close-up view of the pedicle access device docked to a complex facet of the lumbar vertebra;

DETAILED DESCRIPTION OF THE EMBODIMENTS

Figure 3:
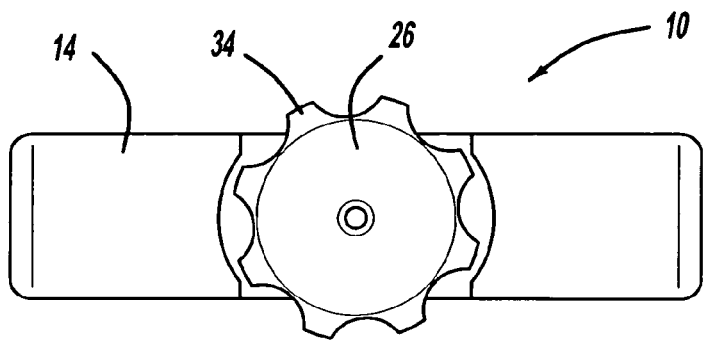
FIG. 3 is a top view of the pedicle access device shown in FIG. 1.

The following discussion of the embodiments of the invention directed to a pedicle access device for spinal fusion surgery is merely exemplary in nature, and is in no way intended to limit the invention or its applications or uses. For example, the pedicle access device of the invention has particular application for targeting a pedicle of a vertebra during spinal fusion surgery. However, as will be appreciated by those skilled in the art, the pedicle access device of the invention may have other applications.

FIG. 1 is a side view of a pedicle access device 10, according to an embodiment of the present invention. The pedicle access device 10 includes a positioning needle 12 having a handle 14 and a hollow rod 16 attached thereto. The pedicle access device 10 further includes a targeting needle 22 including a knob 26 and a rod 28 attached thereto, where the rod 28 of the targeting needle 22 extends through a hollow bore in the rod 16. FIG. 2 is a side view of the targeting needle 22 removed from the positioning needle 12. Further, the handle 14 includes a pair of threaded bores 18 and 20 that accept the threaded end of an elongated handle, as will be discussed in more detail below.

FIG. 3 is a top view of the pedicle access device 10 showing the handle 14 of the positioning needle and the knob 26 of the targeting needle 22. The handle 26 includes a threaded cylindrical portion 32 that threads into a threaded bore (not shown) in the handle 14. The knob 26 includes extended ridges 34 that allow the surgeon to easily grasp the knob 26 during the surgical procedure, and attach or detach the targeting needle 22 to or from the positioning needle 12.

Figure 4:
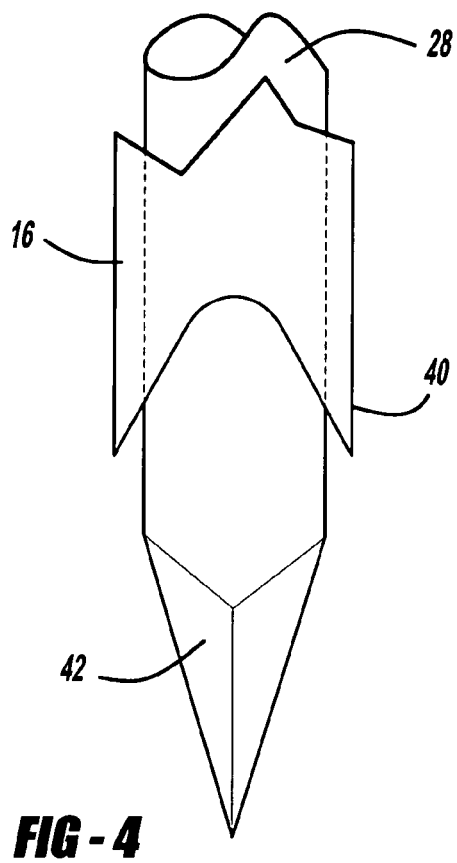
FIGS. 4 and 4a are close-up views of a tip of the pedicle access device shown in FIG. 1.
Figure 4A:
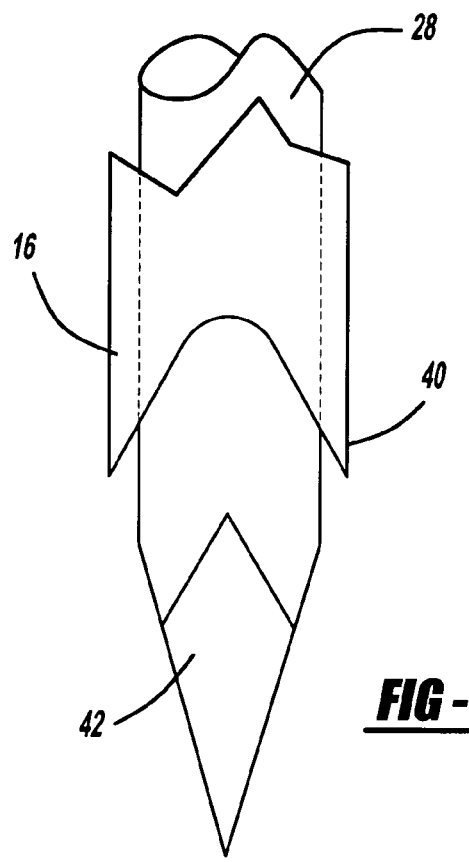
Figure 7:
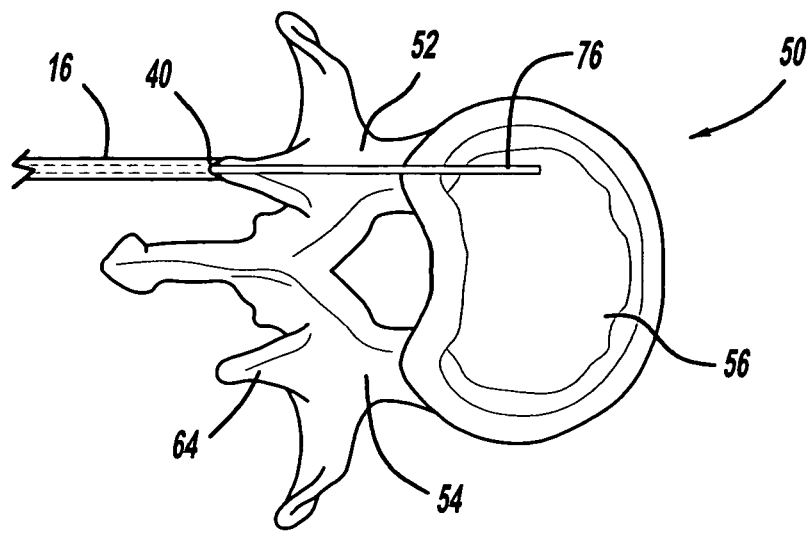
FIG. 7 is a top view of the lumbar vertebra with a K-wire inserted therein.

According to the invention, the positioning needle 12 includes a specially configured tip 40 that allows it to lock onto a complex facet of a vertebra. FIGS. 4 and 4a show a close-up view of the tip 40, also showing a pointed tip 42 of the targeting needle 22 extending therefrom. In this embodiment, the tip 40 of the positioning needle 12 includes opposing conical shape portions that provide the configuration to be secured to the complex facet of the pedicle. In other embodiments, the tip 40 of the positioning needle 12 can have different configurations, such as a saw tooth or corrugated tip, that allow it to reliably dock onto the superior facet. The tip 42 of the targeting needle 22 is very sharp allowing it to sink into the complex facet as the pedicle access device 10 is being moved forward to dock onto the articular process. In one non-limiting embodiment, the tip 42 is a trocar (three-sided) tip.

The materials and dimensions of the various components of the pedicle access device 10 can be any of those suitable for the purposes described herein. In one embodiment, the rods 16 and 28 are stainless steel, and the handles 14 and 26 are a suitable rugged radio-lucent plastic that facilitates viewing of the pedicle during targeting. Further, the length of the pedicle access device is about 7-8 inches. Further, the diameter of the rods 16 and 28 are about 0.25 inches.

FIG. 5 is a perspective view of the pedicle access device 10 positioned relative to a lumbar vertebra 50. The lumbar vertebra 50 includes pedicles 52 and 54 and a vertebral body 56. A spinal canal 60 provides a location to allow the spinal cord to run through the vertebra 50. The tip 42 of the targeting needle 22 is shown docked onto the superior facet 62 of an articular process 64 of the vertebra 50. The pedicle access device 10 is aligned with an axis of the pedicle 52 so that a hole driven through the pedicle 52 and into the vertebral body 56 to accept a pedicle screw is removed from the spinal canal 60.

According to the invention, the pedicle access device 10 also includes an elongated radiation handle 70 that is rigidly coupled to the handle 16. This allows the surgeon to keep his hands out of the surgical field while reducing X-ray exposure. In this embodiment, the handle 70 includes a threaded end (not shown) that is threadably engaged within one of the two threaded holes 18 or 20 in the handle 16. In this manner, the surgeon can hold the pedicle access device 10 relative to the vertebra 50 using the handle 70, and not be exposed to X-rays as they are being taken to see the position of the pedicle access device 10.

Once the surgical area has been prepared and the bone graft material is in place, the surgeon will use fluoroscopy to position the pedicle access device 10 relative to the pedicle to prepare the pedicle for the pedicle screws. The pedicle access device 10 is inserted into the patient so that the tip 42 of the targeting needle 22 docks on the superior articular process of the targeted pedicle. The trajectory of the pedicle access device 10 is then manipulated so that the center of the pedicle is targeted. Once in position, a few gentle taps with a mallet pushes the tip 42 into the pedicle so that the tip 40 engages the pedicle and is docked thereto. A close up orientation of the tips 40 and 42 in this configuration is shown in FIG. 6.

The targeting needle 22 is then removed from the positioning needle 12 and a K-wire 76 is inserted into the rod 16. A K-wire driver (not shown) is then used to drive the K-wire 76 into the pedicle, for example, approximately 0.5-1 cm. The positioning needle 12 is then removed and interial posterior fluoroscopy is performed to ensure that the K-wire 76 is properly positioned. The tip 40 allows the positioning needle 12 to be securely held in place in the pedicle so that the K-wire 76 is properly positioned to reduce injury to the neural elements of the spine. The pedicle access device 10 is easily removed without pulling out the K-wire 76 because the targeting needle 22 is not driven far into the vertebral body 56 as was done with the Jamshidi needle. The positioning needle 12 is then again placed over the K-wire 76, and the K-wire 76 is driven through the pedicle to about one-half the length of the vertebral body 56.

Figure 8:
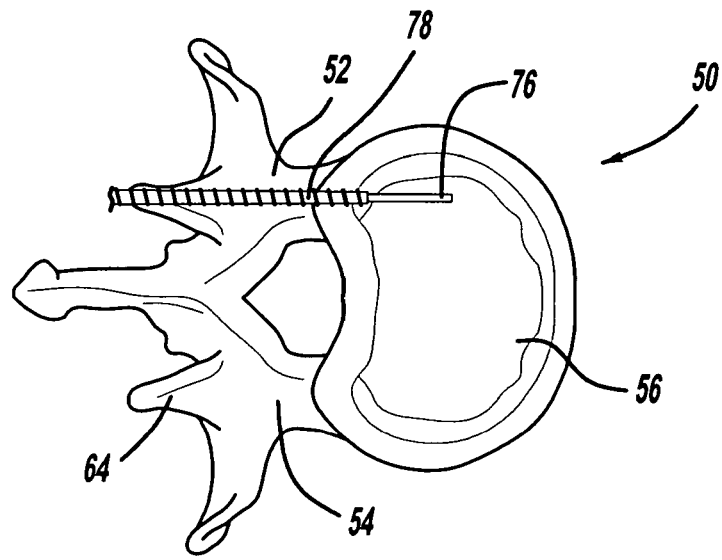
FIG. 8 is a top view of the lumbar vertebra with a cannulated dilator inserted therein.
Figure 9:
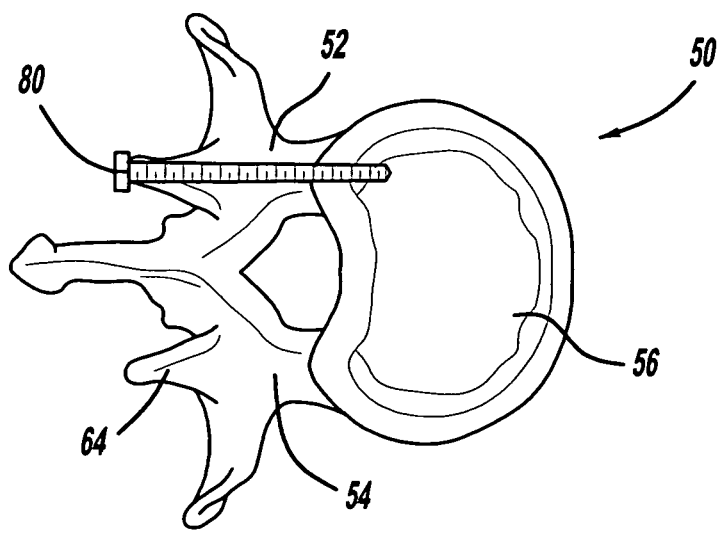
FIG. 9 is a top view of the lumbar vertebra with a pedicle screw inserted therein.

A series of cannulated dilators 78 are used to dilate the muscles and soft tissue around the K-wire 76. A mallet is used to drive the dilators 78 into the vertebra 50. FIG. 8 shows a top view of the vertebra 50 including one of the dilators 78 with the K-wire 76 extending therethrough. Once the hole is large enough, the last dilator 78 is removed from the vertebra 50, the K-wire 76 is removed from the vertebra 50 and the pedicle screw 80 is threaded into the hole in the pedicle and into the vertebral body 56. FIG. 9 is a top view of the vertebra 50 showing the pedicle screw 80 in place.

Each pedicle 52, 54 of adjacent vertebra are prepared in this manner. A pair of bars (not shown) are then mounted to opposing pedicle screws 80 in adjacent vertebra 50 to fuse the vertebrae together by known techniques.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A pedicle access device comprising:
   a positioning needle including a first handle and a hollow tube attached thereto, the hollow tube having a specially configured and shaped end for effectively engaging a facet complex of a vertebra, wherein the specially configured end of the hollow tube has opposing conical configurations, and wherein the opposing conical configurations are conical projections that are separated from each other by opposing recesses having a shape complementary to the facet complex; and
   a targeting needle including a second handle and a rod, the rod extending through the hollow tube of the positioning needle, the second handle being removably secured to said first handle, and wherein a pointed tip of the rod extends out of the specially configured end of the hollow tube.

2. The device according to claim 1 wherein the pointed tip of the rod is a trocar tip.

3. The device according to claim 1 wherein the second handle is removably secured to the first handle by threading a threaded portion of the second handle into a threaded bore of the first handle.

4. The device according to claim 1 wherein the second handle is a knob including extended ridges.

5. The device according to claim 1 further comprising an elongated handle, the elongated handle being coupled to the first handle so as to allow a person to remotely hold the pedicle access device.

6. The device according to claim 5 wherein the elongated handle, the first handle and the second handle are radio-lucent.

7. The device according to claim 5 wherein the elongated handle is threaded to the first handle.

8. The device according to claim 1 wherein the hollow tube and the rod are made of stainless steel and the first and second handles are made of a radio-lucent plastic.

9. The device according to claim 1 wherein the specially configured end of the hollow tube is specially configured to engage the facet complex of an articular process of a vertebra.

10. A pedicle access device comprising a positioning needle including a positioning handle and a hollow tube attached thereto, the hollow tube having a specially configured and shaped end for effectively engaging a facet complex of a vertebra, wherein the specially configured end of the hollow tube has opposing conical portions, and wherein the opposing conical portions are conical projections that are separated from each other by opposing recesses having a shape complementary to the facet complex.

11. The device according to claim 10 further comprising a targeting needle including a knob and a rod, the rod extending through the hollow tube of the positioning needle, the knob being removably secured to the positioning handle by threading a threaded portion of the knob into a threaded bore of the positioning handle, wherein a pointed tip of the rod extends out of the specially configured end of the hollow tube.

12. The device according to claim 11 wherein the pointed tip of the rod is a trocar tip.

13. The device according to claim 11 wherein the knob includes extended ridges.

14. The device according to claim 10 wherein the specially configured end of the hollow tube is specially configured to engage a facet complex of an articular process of a vertebra.

15. The device according to claim 10 further comprising an elongated handle, the elongated handle being coupled to the positioning handle so as to allow a person to remotely hold the pedicle access device.

16. The device according to claim 15 wherein the elongated handle and the positioning handle are radio-lucent.

17. A pedicle access device for docking onto a facet complex of an articular process of a vertebra, the device comprising:
   a positioning needle including a radio-lucent positioning handle and a hollow tube attached thereto, the hollow tube having a specially configured and shaped end for effectively engaging a facet complex of a vertebra, wherein the specially configured end of the hollow tube has opposing conical portions, and wherein the opposing conical portions are conical projections that are separated from each other by opposing recesses having a shape complementary to the facet complex;
   a targeting needle including a radio-lucent knob and a rod, the rod extending through the hollow tube of the positioning needle, the knob being removably secured to the positioning handle by threading a threaded portion of the knob into a threaded bore of the handle, wherein a pointed tip of the rod extends out of the specially configured end of the hollow tube; and a radio-lucent elongated handle, the elongated handle being coupled to the positioning handle so as to allow a person to remotely hold the pedicle access device.

18. The device according to claim 17 wherein the pointed tip of the rod is a trocar tip.

19. A pedicle access device comprising:
a positioning needle including a first handle and a hollow tube attached thereto, the hollow tube having a specially configured and shaped end for effectively engaging a facet complex of a vertebra, wherein the specially configured end of the hollow tube has opposing projections that are separated from each other by opposing recesses having a shape complementary to the facet complex; and
a targeting needle including a second handle and a rod, the rod extending through the hollow tube of the positioning needle, the second handle being removably secured to said first handle, and wherein a pointed tip of the rod extends out of the specially configured end of the hollow tube, wherein the second handle is removably secured to the first handle by threading a threaded portion of the second handle into a threaded bore of the first handle.

20. A pedicle access device comprising a positioning needle including a positioning handle and a hollow tube attached thereto, the hollow tube having a specially configured and shaped end for effectively engaging a facet complex of a vertebra, wherein the specially configured end of the hollow tube has opposing projections that are separated from each other by opposing recesses having a shape complementary to the facet complex; and
a targeting needle including a knob and a rod, the rod extending through the hollow tube of the positioning needle, said knob being removably secured to the positioning handle by threading a threaded portion of the knob into a threaded bore of the positioning handle, wherein a pointed tip of the rod extends out of the specially configured end of the hollow tube.

21. The device according to claim 20 wherein the pointed tip of the rod is a trocar tip.

* * * * *